United States Patent
Bhadra et al.

(10) Patent No.: US 11,446,497 B2
(45) Date of Patent: Sep. 20, 2022

(54) FATIGUING A MUSCLE TO REDUCE ONSET RESPONSE

(71) Applicant: Case Western Reserve University, Cleveland, OH (US)

(72) Inventors: Niloy Bhadra, Richmond Heights, OH (US); Thomas Eggers, Cleveland Heights, OH (US); Kevin L. Kilgore, Avon Lake, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/907,916

(22) Filed: Jun. 22, 2020

(65) Prior Publication Data
US 2021/0052897 A1    Feb. 25, 2021

Related U.S. Application Data

(60) Provisional application No. 62/889,064, filed on Aug. 20, 2019.

(51) Int. Cl.
*A61N 1/36* (2006.01)
*A61N 1/05* (2006.01)

(52) U.S. Cl.
CPC ....... *A61N 1/36067* (2013.01); *A61N 1/0556* (2013.01); *A61N 1/36003* (2013.01); *A61N 1/36121* (2013.01)

(58) Field of Classification Search
CPC .............. A61N 1/0556; A61N 1/36003; A61N 1/36067; A61N 1/36121; A61N 1/0551; A61N 1/36071; A61N 1/36171; A61N 1/36175; A61N 1/36178; A61N 1/36192; A61N 1/36196
See application file for complete search history.

(56) References Cited

U.S. PATENT DOCUMENTS

| | | |
|---|---|---|
| 6,295,472 B1 | 9/2001 | Rubinstein et al. |
| 6,631,295 B2 | 10/2003 | Rubinstein et al. |
| 6,721,603 B2 | 4/2004 | Zabara et al. |

(Continued)

OTHER PUBLICATIONS

Bhadra, Niloy, and Kevin L Kilgore. "High-frequency electrical conduction block of mammalian peripheral motor nerve." Muscle & nerve vol. 32,6 (2005): 782-90. (Year: 2005).*

(Continued)

*Primary Examiner* — Carl H Layno
*Assistant Examiner* — Anh-Khoa N Dinh
(74) *Attorney, Agent, or Firm* — Tarolli, Sundheim, Covell & Tummino LLP

(57) ABSTRACT

The occurrence of negative consequences (e.g., painful tetanic muscle contractions) associated with the onset response associated with kilohertz frequency alternating current (KHFAC) electrical nerve block can be reduced by fatiguing a muscle (through depletion of neurotransmitters at the neuromuscular junction, within a second) before applying KHFAC electrical nerve block to a nerve associated with the muscle. The nerve can first be stimulated with an electrical signal for a first time period to fatigue the muscle. Then, immediately following the first time period (while the muscle is fatigued), a blocking electrical signal (e.g., a kilohertz frequency alternating current waveform) can be applied to the nerve to create a localized nerve block.

12 Claims, 5 Drawing Sheets

(56) References Cited

U.S. PATENT DOCUMENTS

| | | | |
|---|---|---|---|
| 9,393,411 B2 | 7/2016 | Bhadra et al. | |
| 10,758,728 B2 | 9/2020 | Tyler et al. | |
| 2006/0184211 A1* | 8/2006 | Gaunt | A61N 1/05 607/48 |
| 2010/0241190 A1* | 9/2010 | Kilgore | A61N 1/205 607/48 |
| 2015/0202441 A1* | 7/2015 | Franke | A61N 1/36067 606/34 |
| 2016/0001082 A1* | 1/2016 | Butera | A61N 1/36057 607/66 |
| 2018/0050205 A1 | 2/2018 | Moffitt et al. | |
| 2019/0015663 A1 | 1/2019 | Bennett et al. | |

OTHER PUBLICATIONS

Bhadra, Niloy, and Kevin L. Kilgore. "High-frequency electrical conduction block of mammalian peripheral motor nerve." Muscle & Nerve: Official Journal of the American Association of Electrodiagnostic Medicine 32.6 (2005): 782-790.

Chakravarthy, Krishnan, et al. "Spinal cord stimulation for treating chronic pain: reviewing preclinical and clinical data on paresthesia-free high-frequency therapy." Neuromodulation: Technology at the Neural Interface 21.1 (2018): 10-18.

Corriveau, Mark, Wendell Lake, and Amgad Hanna. "Nerve stimulation for pain." Neurosurgery Clinics 30.2 (2019): 257-264.

Graczyk, Emily L., et al. "The neural basis of perceived intensity in natural and artificial touch." Science translational medicine 8.362 (2016): 362ra142-362ra142.

Guan, Yun, et al. "Spinal Cord Stimulation: Mechanisms of Action." Neuromodulation. Academic Press, 2018. 161-178.

Huntoon, Marc A., and Abram H. Burgher. "Ultrasound-guided permanent implantation of peripheral nerve stimulation (PNS) system for neuropathic pain of the extremities: original cases and outcomes." Pain Medicine 10.8 (2009): 1369-1377.

Navarro, Xavier, et al. "A critical review of interfaces with the peripheral nervous system for the control of neuroprostheses and hybrid bionic systems." Journal of the Peripheral Nervous System 10.3 (2005): 229-258.

Rubenstein, J. T., et al. "Pseudospontaneous activity: stochastic independence of auditory nerve fibers with electrical stimulation." Hearing research 127.1-2 (1999): 108-118.

Slavin, Konstantin V. "Peripheral nerve stimulation for neuropathic pain." Neurotherapeutics 5.1 (2008): 100-106.

Tan, Daniel, et al. "Intensity modulation: a novel approach to percept control in spinal cord stimulation." Neuromodulation: Technology at the Neural Interface 19.3 (2016): 254-259.

Tyler, Richard S., et al. "Electrical stimulation of the cochlea to reduce tinnitus." Seminars in Hearing. vol. 29. No. 4. NIH Public Access, 2008.

Vlassakov, Kamen V., Sanjeet Narang, and Igor Kissin. "Local anesthetic blockade of peripheral nerves for treatment of neuralgias: systematic analysis." Anesthesia & Analgesia 112.6 (2011): 1487-1493.

* cited by examiner

FATIGUING A MUSCLE TO REDUCE ONSET RESPONSE

CLAIM OF PRIORITY

This application claims priority to U.S. Provisional Application Ser. No. 62/889,064, filed Aug. 20, 2019, entitled "FATIGUING THE MUSCLE TO REDUCE THE ONSET RESPONSE DUE TO KILOHERTZ FREQUENCY ALTERNATING CURRENT". The entirety of this provisional application is hereby incorporated by reference for all purposes.

GOVERNMENT SUPPORT

This invention was made with government support under R01-EB-024860 awarded by the National Institutes of Health. The government has certain rights in the invention.

TECHNICAL FIELD

The present disclosure relates generally to electrical nerve block and, more specifically, to systems and methods that can reduce painful muscle contractions associated with the onset response associated with kilohertz frequency alternating current (KHFAC) electrical nerve block by fatiguing a muscle before applying the KHFAC block.

BACKGROUND

Implanted electrodes can implement immediate and reversible electrical nerve block safely and effectively. Kilohertz frequency alternating current (KHFAC) is a type of electrical nerve block that can maintain nerve block for hours safely, and potentially continuously. However, KHFAC suffers from a phenomenon known as the onset response—a period of intense neural activation, which can last anywhere from less than 1 second to greater than 30 seconds. During the onset response, patients can experience painful muscle contractions (e.g., tetanic muscle contractions due to the onset response), making the onset response a large hurdle in translating KHFAC electrical nerve block to clinical practice.

SUMMARY

Provided herein is a solution that can reduce the occurrence of painful muscle contractions associated with the onset response associated with the initiation of kilohertz alternating current (KHFAC) electrical nerve block. Described herein are systems and methods that can fatigue a muscle (through depletion of neurotransmitters at the neuromuscular junction, within a second) before applying KHFAC electrical nerve block.

In one aspect, the present disclosure can include a system that can avoid an onset response characteristic of electrical nerve block (e.g., KHFAC nerve block). The system can include a waveform generator configured to generate a fatigue block waveform, which includes a fatigue alternating current waveform with a first frequency for a first time period, and a block alternating current waveform with a second frequency (greater than the first frequency) immediately after the first time period. The system can also include an electrode contact coupled to the waveform generator. The electrode contact can be configured to apply the fatigue alternating current waveform to a nerve for the first time period. A muscle can become fatigued due to stimulating the nerve with the fatigue alternating current waveform. The electrode contact can be configured to apply the blocking waveform to a nerve to create a localized nerve block, after the first time period. Since the muscle is fatigued during initial application of the blocking waveform (e.g., a KHFAC waveform), the muscle does not experience the painful muscle contractions associated with the onset response.

In another aspect, the present disclosure can include a method for avoiding an onset response characteristic of electrical nerve block (e.g., KHFAC nerve block). A nerve (associated with a muscle) can be stimulated with an electrical signal for a first time period to fatigue the muscle. Immediately after the first time period (while the muscle is fatigued), a blocking electrical signal can be applied to the nerve to create a localized nerve block. The blocking electrical signal can include a KHFAC waveform. Since the muscle is fatigued during initial application of the KHFAC waveform, the muscle does not experience the painful muscle contractions associated with the onset response.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
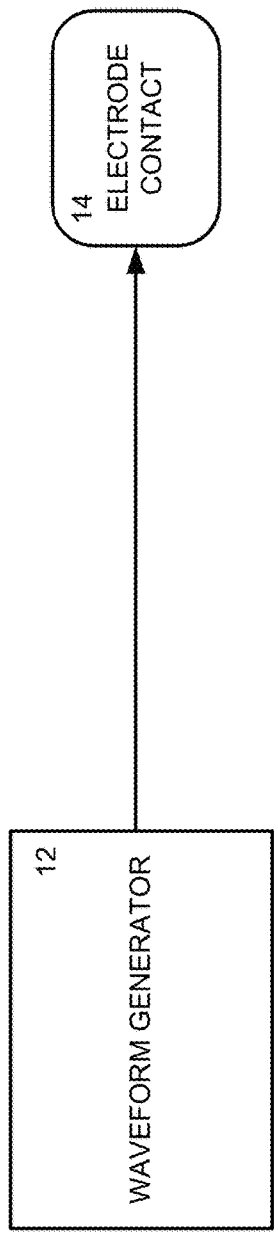
FIG. 1 is a diagram showing an example of a system that can be used to reduce painful muscle contractions associated with the onset response associated with kilohertz frequency alternating current (KHFAC) electrical nerve block.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the term "onset response" refers to a period (lasting anywhere from less than 1 second to greater than 30 seconds) of intense neural activation (or intense signaling) when kilohertz frequency alternating current (KHFAC) electrical nerve block is first initiated. During the onset response, a nerve can conduct in an overactive manner for a short period of time. Spastic patients can experience painful muscle contractions (tetanic muscle contractions induced by the overactive conduction of the onset response) in spastic muscles during the onset response, for example.

As used herein, the term "KHFAC electrical nerve block" can refer to a block of conduction (also referred to as signaling) in a nerve (which can be partial or complete) using a KHFAC waveform. KHFAC electrical nerve block has been shown to produce a rapid and reversible block of nerve conduction.

As used herein, the term "tetanic muscle contraction" can refer to an involuntary, sustained, and often painful skeletal muscle contraction due to repetitive signaling by a motor nerve that innervates a motor unit containing skeletal muscle fibers and conducts at a high rate.

As used herein, the term "nerve" can refer to a "motor neuron", a nerve cell carrying impulses from the brain or spinal cord to a muscle or gland. A motor neuron can form a motor unit with one or more muscle fibers.

As used herein, the term "muscle" can refer to one or more muscle fibers that has the ability to contract. The one or more muscle fibers can form a motor unit with a motor neuron. The term muscle can refer to skeletal muscle.

As used herein, the term "fatigue" can refer to muscle fatigue, a decrease in a muscle's ability to generate force. Fatigue can be due to depletion of neurotransmitters at the neuromuscular junction (NMJ) or by metabolic fatigue of the muscle fibers themselves. As used herein, "fatigue" refers to depletion of neurotransmitters at the NMJ and can occur within a second.

As used herein, the term "electrode contact" can refer to a material acting as a conductor through which electricity enters or leaves. At least a portion of the material can be a biocompatible material. An electrode can include one or more electrode contacts.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

Electrical nerve block, such as kilohertz frequency alternating current (KHFAC) electrical nerve block, can be used to maintain a nerve block for hours safely and effectively. However, KHFAC electrical nerve block has not transitioned to clinical practice because KHFAC suffers from a phenomenon known as the onset response during which patients can experience painful muscle contractions. Provided herein is a solution that does not stop the nerve conduction associated with the onset response, but can reduce the occurrence of the associated painful muscle contractions.

Described herein are systems and methods that can fatigue a muscle (through depletion of neurotransmitters at the neuromuscular junction, within a second) before applying KHFAC electrical nerve block. The muscle can be fatigued by providing a brief period of stimulation to fatigue the muscle (e.g., the stimulation waveform can have a frequency of 1 kHz, which can fatigue the muscle in <1 s) before initiating the KHFAC (e.g., with a frequency of 20 kHz, which creates a localized nerve block) for the KHFAC nerve block. Thus, the muscle still receives the onset activity from the nerve, but the muscle is unable to generate the painful tetanic muscle contractions due to being in a fatigued state. This technique could be used in humans suffering from spasticity where large muscle contractions associated with the onset response would prove to be painful and potentially damaging to the patients' arm/leg.

III. System

A safe, effective block of nerve conduction can be provided for hours using an electrical nerve block, such as kilohertz frequency alternating current (KHFAC) electrical nerve block. However, KHFAC electrical nerve block has not been adopted in clinical practice, for treatment of conditions like muscle spasticity, because KHFAC electrical nerve block suffers from a phenomenon known as the onset response during which patients can experience painful muscle contractions. If these painful muscle contractions can be minimized and/or stopped, KHFAC block would provide a stable, long term electrical nerve block solution that can be used to treat conditions like muscle spasticity (e.g., associated with one or more muscles associated with at least one of a patient's arms and/or legs). Currently, the pain (and potential for damage) of the onset response (especially associated with large muscle groups experiencing spasticity) outweighs the utility of the KHFAC block. The system 10 (FIG. 1) provides a solution that does not stop the nerve conduction associated with the onset response, but can reduce the occurrence of the associated painful muscle contractions.

The system 10 includes a waveform generator 12 and an electrode contact 14. The waveform generator 12 can be configured to generate a Fatigue Block Waveform. The Fatigue Block Waveform can (1) provide a Fatigue Waveform to the nerve to fatigue a muscle (through depletion of neurotransmitters at the neuromuscular junction, within a second) and (2) apply a Blocking Waveform (a KHFAC electrical nerve block) that still has the onset response, but does not cause the fatigued muscle to contract during the onset response. The Fatigue Block Waveform can be delivered to the electrode contact 14 through a wired connection and/or a wireless connection.

The Fatigue Waveform, also referred to as a stimulation waveform can be applied to the nerve innervating the muscle to provide a brief period of stimulation. The stimulated nerve can release neurotransmitter to activate the muscle to contract (e.g., a tetanic muscle contraction) and this neurotransmitter can fatigue the muscle (so that the muscle cannot contract for a period of time, even when receiving a neural stimulus, referred to as neuromuscular junction fatigue). The muscle can be fatigued even with the brief period of stimulation of the nerve.

The Fatigue Waveform can be provided by any charge balanced waveform, including, but not limited to, a continuous waveform (e.g., sinusoidal, square, triangle, etc.), as well as any type of discontinuous waveform (e.g., charge balanced square pulses with gaps between each individual charge balanced pulse pair). One example application includes the Fatigue Waveform as an alternating current with an amplitude (e.g., a value sufficient to stimulate the nerve)

and a frequency from 500 Hz to 2 kHz (e.g., less than or equal to 1 kHz). By stimulating the nerve for a short time period, the muscle can be quickly fatigued. The short time period can be less than 10 seconds, less than 5 seconds, less than 3 seconds, 1 second or less, or the like. As one example, the Fatigue Waveform can be applied to the nerve for 3 seconds at a frequency of 1 kHz to fatigue the muscle.

Immediately after the time period of the Fatigue Waveform, the waveform generator 12 can increase the frequency and provide the Blocking Waveform (which can be configured as a KHFAC waveform). The Blocking Waveform can have a frequency greater than 1 kHz (so that the Blocking Waveform has a greater frequency than the Fatigue Waveform). In some instances, the frequency of the Blocking Waveform can be greater than 1 kHz, but less than 50 kHz. As an example, the frequency of the Blocking Waveform can be 20 kHz. In its simplest form, the Blocking Waveform can have the same amplitude as the Fatigue Waveform (so that the only change is the frequency). However, the amplitude may also change between the Fatigue Waveform and the Blocking Waveform. Notably, for when the Blocking Waveform is turned on, an onset response is still produced by the nerve and the nerve still signals the muscle. However, the muscle is fatigued and unable to activate and contract to provide the painful muscle contraction associated with the onset response.

The Fatigue Block Waveform can be delivered by the waveform generator 12 to the electrode contact 14, which can apply the Fatigue Block Waveform to the nerve. The electrode contact 14 can be configured to first apply the Fatigue Waveform to the nerve to fatigue the muscle. Then, immediately after a time period of the Fatigue Waveform, the electrode contact 14 can apply the Blocking Waveform (which can be applied for a second time period when the muscle is fatigued and the nerve generates the onset response (e.g., less than 1 minute) and a third time period when the onset response is over and the muscle is no longer fatigued).

The electrode contact 14 can include a conductive metal and/or polymer shaped or sized to facilitate delivery of the Fatigue Block Waveform to the nerve. The electrode contact 14 in some instances can include more than one electrode contact (e.g., one electrode contact applies the Fatigue Waveform, another contact applies the Block Waveform). Additionally, it is possible to apply the Fatigue Block Waveform by one or more electrode contacts in a first electrode and the Block Waveform by another on or more contacts in a second electrode.

Figure 2:
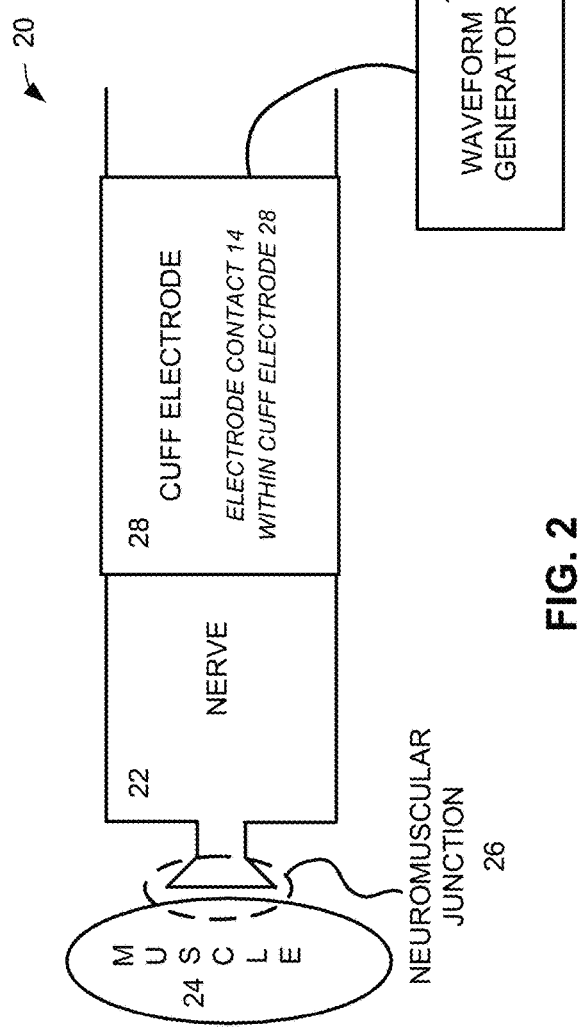
FIG. 2 is a diagram showing an example implementation of the system of FIG. 1.

Shown in FIG. 2 is an example 20 implementation of the system 10. The waveform generator 12 is coupled to at least one electrode contact 14, which is found within a nerve cuff (or cuff electrode) 28. The cuff electrode 28 can be located far enough down the nerve so as not to interfere with the neuromuscular junction 26 between a synapse of the nerve 22 and a receptor of the muscle 24.

The waveform generator 12 can generate the Fatigue Block Waveform and send the Fatigue Block Waveform to the electrode contact 14. The electrode contact 14, within the cuff electrode 28, applies Fatigue Block Waveform to the nerve 22. During Fatigue Waveform, the nerve 22 activates the muscle 24 until the muscle 24 is fatigued. Immediately after the Fatigue Waveform, the Block Waveform is sent to the nerve 22. An onset response occurs in the nerve 22 in response to the Bock Waveform, the nerve 22 releases neurotransmitters at the neuromuscular junction 26, but the muscle 24 (being fatigued) is unable to contract. After the fatigue wears off, the muscle 24 still does not contract because nerve conduction is now blocked.

IV. Methods

Figure 3:
FIGS. 3-4 are process flow diagrams showing example methods for reducing painful muscle contractions associated with the onset response associated with KHFAC electrical nerve block.
Figure 4:

Another aspect of the present disclosure can include methods 30-40, as shown in FIGS. 3-4, for reducing painful muscle contractions associated with the onset response associated with kilohertz frequency alternating current (KHFAC) electrical nerve block. The methods 30-40 can reduce the onset response to by fatiguing a muscle (through depletion of neurotransmitters at the neuromuscular junction, within a second) before applying the KHFAC block. The methods 30-40 can be performed by the system of FIG. 1, as shown and described further in FIG. 2.

The methods 30-40 are illustrated as a process flow diagram with flow chart illustrations. For purposes of simplicity, the methods are shown and described as being executed serially; however, it is to be understood and appreciated that the present disclosure is not limited by the illustrated order, as some steps could occur in different orders and/or concurrently with other steps shown and described herein. Moreover, not all illustrated aspects may be required to implement the methods.

Referring now to FIG. 3, illustrated is a method 30 for reducing painful muscle contractions associated with the onset response associated with KHFAC electrical nerve block. Using the method 30, a Fatigue Block Waveform can be applied to a nerve to (1) fatigue a muscle associated with the nerve (through fatigue of the neuromuscular junction) and (2) block conduction in the nerve.

At 32, a nerve can be stimulated with an electrical signal for a first time period to fatigue a muscle. The first time period can be relatively short (e.g., shorter than the second time period and the third time period). The patient should not be able to perceive the fatiguing electrical signal, in some instances. For example, the first time can be less than 3 seconds. As another example, the first time can be less than 1 second. The electrical signal can have an amplitude and a frequency sufficient to cause a fast fatigue of the muscle. The muscle can be associated with a nerve at a neuromuscular junction as shown in FIG. 2. The Fatigue Waveform can be provided by any charge balanced waveform, including, but not limited to, a continuous waveform (e.g., sinusoidal, square, triangle, etc.), as well as any type of discontinuous waveform (e.g., charge balanced square pulses with gaps between each individual charge balanced pulse pair). One example application includes the Fatigue Waveform as an alternating current with an amplitude (e.g., a value sufficient to stimulate the nerve) and a frequency from 500 Hz to 2 kHz (e.g., less than or equal to 1 kHz).

At 34, after the first time period, a blocking electrical signal (e.g., a KHFAC waveform, frequency greater than or equal to 1 kHz with an amplitude sufficient to cause block, which may be the same as the amplitude of the electrical signal) can be immediately applied to create a localized nerve block. The localized nerve block can be utilized to treat a neurological condition associated with a neuromuscular junction. As one example, the neurological condition can be muscle spasticity associated with at least one muscle of the patient's arm and/or leg.

As shown in FIG. 4, an onset response is still generated (at 42) when the KHFAC waveform is delivered to the nerve. However, because the muscle is fatigued, the muscle does not have a muscle contraction in response to the onset response (at 44). The electrical signal is designed to fatigue the muscle so that the muscle remains fatigued during a second period of time when the blocking electrical signal is applied. The blocking electrical signal causes the nerve to generate onset activity and send the onset activity to the muscle, but since the muscle remains fatigued, the muscle is unable to generate at least one muscle contraction in response to the onset activity. The KHFAC waveform can continue to block the conduction in the nerve for a third period of time after the muscle recovers from fatigue and after the onset response. The third period of time can be longer than both the first period of time and the second period of time. As an example, the third period of time can be twenty minutes. As another example, the third period of time can be sixty minutes. As a further example, the third period of time can be three hours. The third period of time can be any length of time from 5 minutes to several hours, even days.

V. Experimental

The following example shows an experimental use of a Fatigue Block Waveform (shown in FIG. 5) to stop the onset response by (1) fatiguing a muscle associated with a nerve (through depletion of neurotransmitters at the neuromuscular junction, within a second) using an AC waveform and (2) blocking conduction in the nerve with a kilohertz frequency alternating current (KHFAC) waveform. The following example is for the purpose of illustration only and is not intended to limit the appended claims.

Methods

Figure 5:
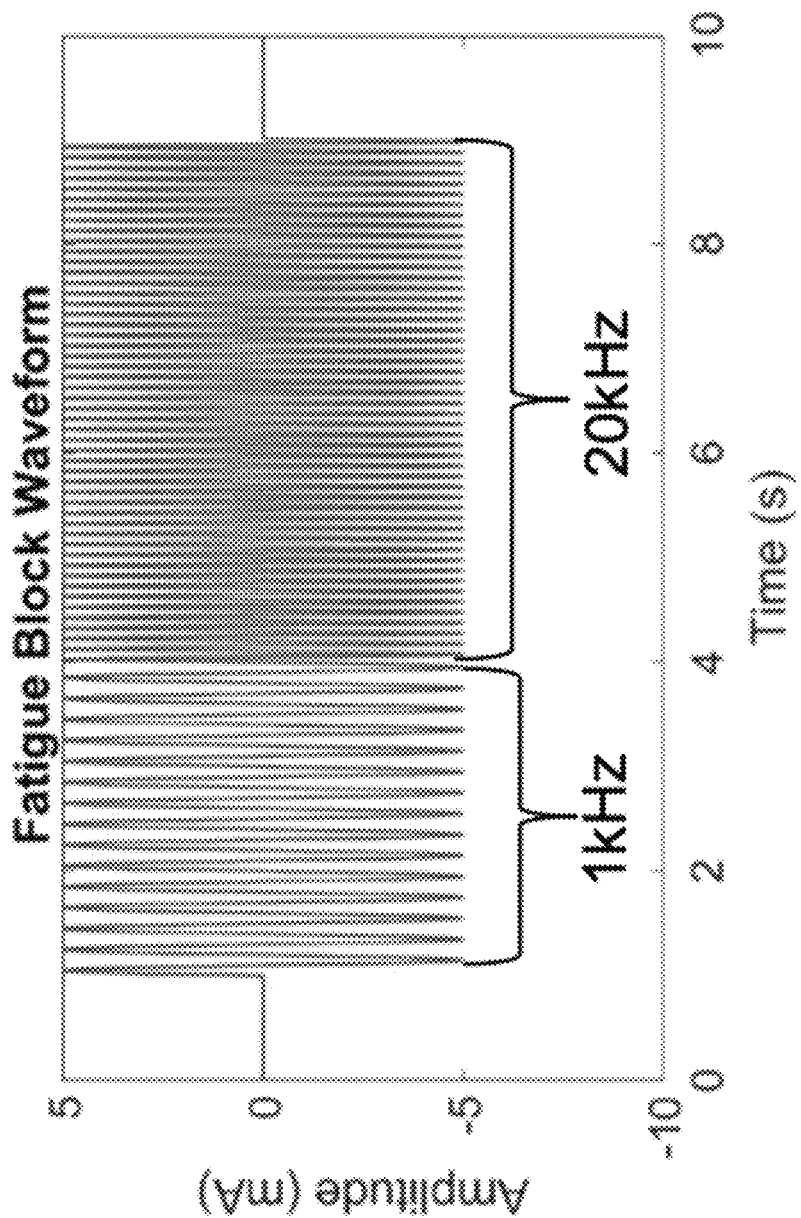
FIG. 5 is a diagram showing an example implementation of a Fatigue Block Waveform.

FIG. 5 shows an example diagram of the Fatigue Block Waveform. For the first several seconds, a sinusoid is applied at an amplitude and with a frequency of 1 kHz (a Fatigue waveform). Then the frequency of the sinusoid is increased to 20 kHz (a KHFAC blocking waveform) to block conduction in the nerve. In theory, the Fatigue waveform should fatigue the muscle so that the muscle does not experience an inset response when the KHFAC blocking waveform is turned on.

Figure 6:
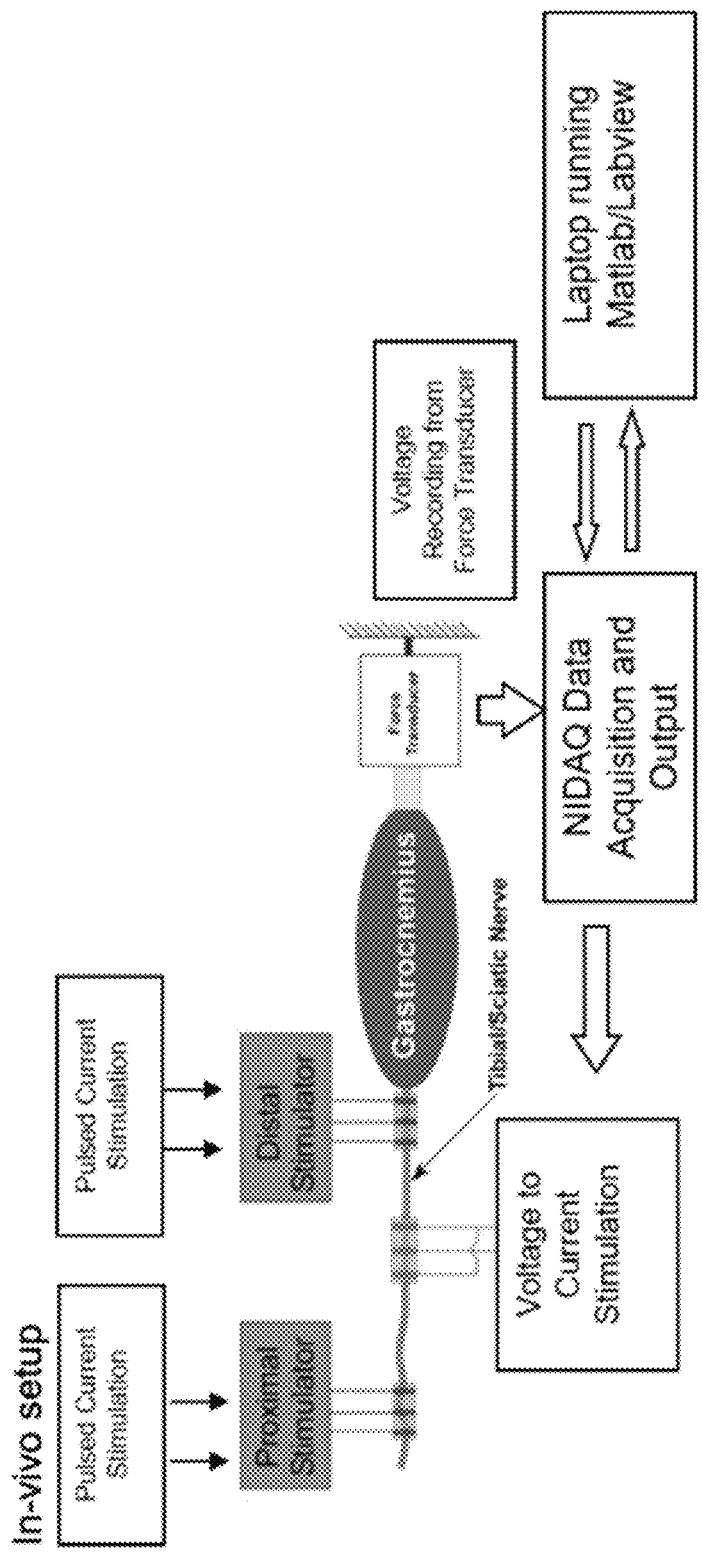
FIG. 6 is a diagram showing an example in vivo experimental setup used to test the Fatigue Block Waveform.
Figure 7:
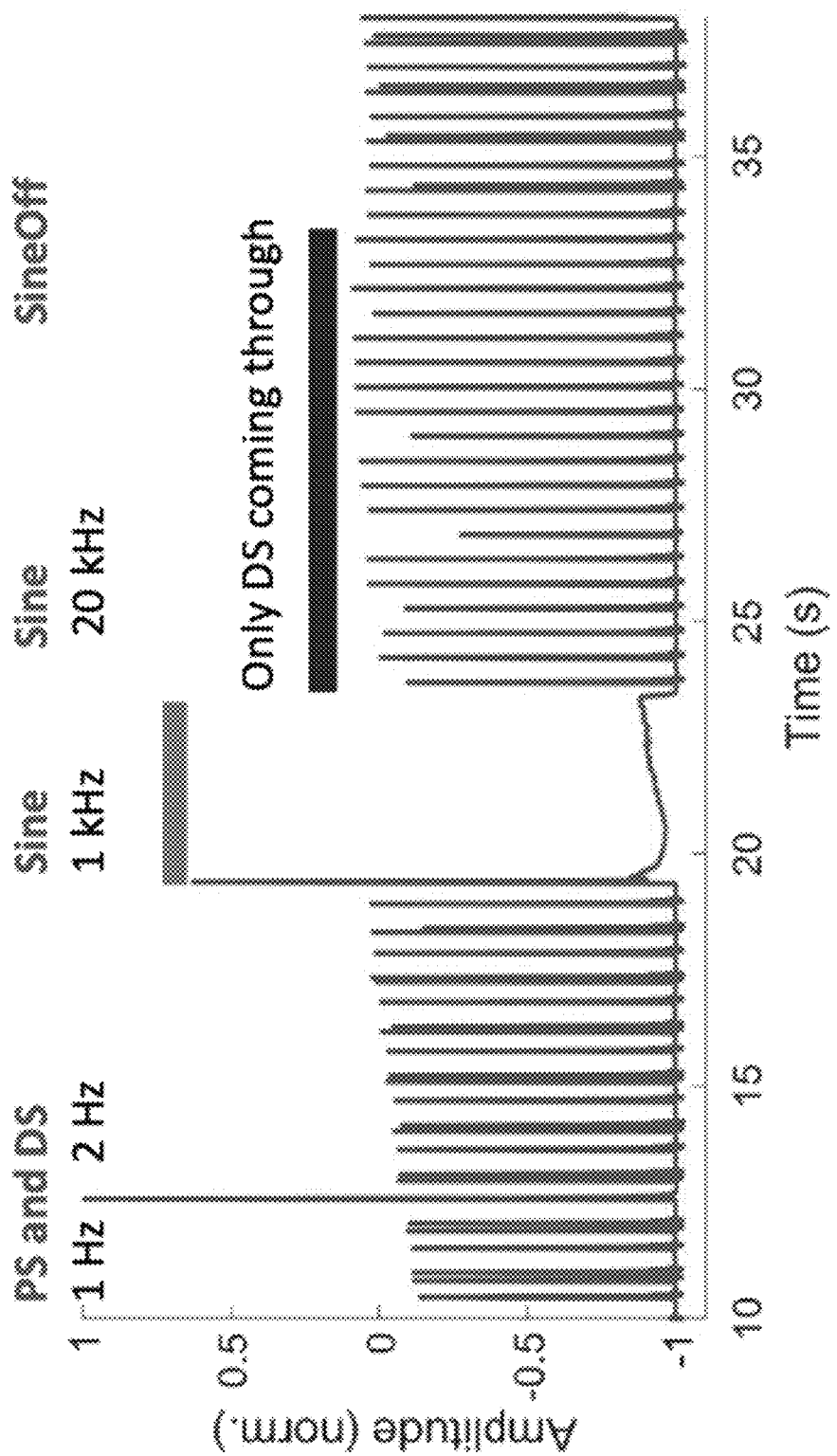
FIG. 7 is a plot showing experimental results from in vivo testing of the Fatigue Block Waveform.

FIG. 6 is a schematic diagram of an in vivo setup for testing an acute rat model (the gastrocnemius muscle). The fatigue waveform was generated in MATLAB software with a custom script, generating a text file. LABVIEW software then read this file and generated an analog voltage signal via the NIDAQ, and this voltage was converted to a current with the voltage to current stimulator. This current was then sent to a tripolar cuff (as shown in FIG. 6) or to a bipolar electrode or a monopolar cuff with a distant return (not shown).

To test for block, the proximal stimulation was started, eliciting twitches from the Gastrocnemius muscle which were read by the force transducer. The block was then turned on, and the loss of twitches indicated block had occurred. Distal stimulation was used to measure nerve damage by comparing the force between distal and proximal stimulation.

Results

FIG. 8 shows the force produced by the gastrocnemius due to the fatigue block waveform on the sciatic nerve. The proximal stimulation (PS) and distal stimulation (DS) remained on throughout the entire trial at 1 Hz and 2 Hz, respectively. At the beginning and end of the trial, both sets of stimulation were present. Once the 1 kHz sine is initiated (the fatigue waveform), neither the proximal nor distal stimulation appeared, showing that the muscle was fatigued at the neuromuscular junction. Once the sine wave was transitioned to 20 kHz (the blocking waveform), the DS comes through, demonstrating a localized nerve block.

Importantly, no new onset was observed at the transition from 1 kHz to 20 kHz; only the first initial twitch followed by a low level of static activation is observed. Accordingly, the Fatigue Block Waveform can decrease the onset response in muscles and still create a localized nerve block.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The invention claimed is:

1. A method comprising:
   stimulating a nerve by applying an electrical signal comprising a fatigue alternating current waveform with a first frequency that is 1 kHz or less for a first time period of 3 seconds or less to the nerve to fatigue a muscle, wherein the muscle is associated with the nerve; and
   after the first time period, immediately applying a blocking electrical signal to the nerve to create a localized nerve block while the muscle remains fatigued, wherein the blocking electrical signal comprises a kilohertz frequency alternating current waveform having a second frequency greater than 1 kHz.

2. The method of claim 1, wherein the blocking electrical signal causes the nerve to generate onset activity and send the onset activity to the muscle, but since the muscle remains fatigued, the muscle is unable to generate at least one muscle contraction in response to the onset activity.

3. The method of claim 2, wherein the kilohertz frequency alternating current waveform blocks conduction in the nerve to treat a neurological condition for a third time period after the onset activity and after the muscle is no longer fatigued.

4. The method of claim 3, wherein the neurological condition is muscle spasticity associated with at least one muscle of a patient's arm and/or leg.

5. The method of claim 1, wherein the first time period comprises 1 second or less.

6. A system comprising:
   a waveform generator configured to generate a fatigue block waveform, wherein the fatigue block waveform comprises:
      a fatigue alternating current waveform with a first frequency of 1 kHz or less for a first time period of 3 seconds or less; and
      a block alternating current waveform with a second frequency of 1 kHz or more immediately after the first time period; and
   an electrode contact configured to apply the fatigue alternating current waveform to a nerve for the first time period to fatigue a muscle associated with the nerve, and to apply the blocking waveform to the nerve immediately after the first time period to create a localized nerve block while the muscle remains fatigued.

7. The system of claim 6, wherein the electrode contact is part of a cuff electrode in communication with the nerve.

8. The system of claim 6, wherein the blocking waveform causes the nerve to generate onset activity and send the onset activity to the muscle, but the muscle is unable to generate at least one muscle contraction in response to the onset activity due to the fatigue.

9. The system of claim 8, wherein the blocking waveform blocks nerve conduction related to a neurological condition for a third period of time after the onset activity and after the fatigue resolves.

10. The system of claim 9, wherein the neurological condition is muscle spasticity associated with at least one muscle of a patient's arm and/or leg.

11. The system of claim 6, wherein the blocking waveform comprises a kilohertz frequency alternating current waveform.

12. The system of claim 6, wherein the first time period comprises 1 second or less.

\* \* \* \* \*